United States Patent [19]
Sung et al.

[11] Patent Number: 5,925,537
[45] Date of Patent: Jul. 20, 1999

[54] PROCESS FOR THE PREPARATION OF METABOLITES OF *GINSENG SAPONINS*

[75] Inventors: Jong Hwan Sung; Jae Doo Huh, both of Kyonggi-do, Rep. of Korea; Hideo Hasegawa, Tokyo; Satoshi Matsumiya, Tokyo; Masamori Uchiyama, Tokyo, all of Japan

[73] Assignees: Il Hwa Co., Ltd., Guri-si, Rep. of Korea; Happy World Inc., Tokyo, Japan

[21] Appl. No.: 08/982,260

[22] Filed: Dec. 1, 1997

[30] Foreign Application Priority Data

Nov. 29, 1996 [KR] Rep. of Korea ........................ 96-59368

[51] Int. Cl.$^6$ .............................. C12N 1/20; C12P 33/20; A01N 65/00
[52] U.S. Cl. .............................. 435/53; 435/71.2; 435/74; 435/252.1; 424/195.1; 514/26; 536/5
[58] Field of Search ........................... 435/74, 53, 252.1, 435/71.2; 536/5; 514/26; 424/195.1

[56] References Cited

FOREIGN PATENT DOCUMENTS

4217/1996 12/1995 Rep. of Korea .

OTHER PUBLICATIONS

Chemical Pharm. Bull., Yostoea et al, Soil Bacteria Hydrolysis Leading to Genuine Aglycone V . . . , pp. 2418–2421, 1972.

Yakugaku Zasshi, Kohda et al, Enzymatic Hydrolysis of Saponins and Their Related Glycosides, pp. 246–249, 1975.

Medicinal Ginseng, "Ginsenoside Rb$_2$", pp. 246–278, 1989.

Journal of Traditional Medicinen, Kanaoka et al, "Metabolism of Ginsing Saponins . . . ", pp. 241–245, 1994.

Bergey's Manual of Systemic Bacteriology, pp. 616–617, 1984.

Int'l. Journal of Systematic Bacteriol, Shah et al, Prevotella, a New Genus To Include Bacteroides . . . , pp. 205–208, 1990.

Chemical Computer Abstract CA127:275173 Hasegawa et al "Role of human intestinal *Prevotella oris* in hydrolyzing ginseng saponins" Planta Med. (1997) 65(5) pp. 436–440.

*Primary Examiner*—Herbert J. Lilling
*Attorney, Agent, or Firm*—Jacobson, Price, Holman & Stern, PLLC

[57] ABSTRACT

According to this invention, Prevotella sp. S-1 strain (Bacteroidaceae family, KFCC-10923) is cultured in a medium supplemented with Panax ginseng saponin so as to collect the metabolites of saponin generated and accumulated in the medium, thus ensuring their selective production with high efficiency.

This invention related to a process for the preparation of the metabolites of protopanaxadiol saponin, wherein Prevotella sp. S-1 strain (Bacteroidaceae family, KFCC-10923), is cultured at a medium supplemented with Panax ginseng saponin and then, the metabolites of protopanaxadiol saponin contained in the medium—20-O-β-D-glucopyranosyl-20(s)-protopanaxadiol, 20-O-[α-L-arabinopyranosyl-20(s)-protopanaxadiol, and 20-0-[α-L-arabinopuranosyl(1→6)-β-D-glucopyranosyl]-20(s)-protopanaxadiol —are generated and accumulated for collecting them thereof.

6 Claims, No Drawings

PROCESS FOR THE PREPARATION OF METABOLITES OF *GINSENG SAPONINS*

FIELD OF THE INVENTION

This invention relates to a process for the preparation of metabolites of protopanaxadiol saponins, being collected from the following procedure that Prevotella sp. S-1 strain (Bacteroidaceae family, KFCC-10923 and it's converted into the accession number KCCM-10103 under Budapest Treaty) is cultured at a medium supplemented with Panax ginseng saponin and then, protopanaxadiol saponin contained in the medium is generated and accumulated for the embodiment of this invention.

BACKGROUND OF THE INVENTION

Korean Panax ginseng has long been regarded as a valuable panacea in the treatment of some physical disorders due to its various therapeutic effects. When Panax ginseng is intended for use in the treatment of various diseases, however, its shortcomings are that a) saponin, a therapeutic ingredient, is metabolized by intestinal bacteria, and b) since the intestinal bacteria groups are susceptible to person's physical constitution and his lifestyle of foods, there is a possibility that an individual differences in a saponin metabolism may occur, thus affecting the therapeutic effects in the long run. To comply with this matter, the inventors have extensively studied the therapeutic effects on the metabolites of Panax saponins in the body, and have come to know that the saponins metabolized by intestinal bacteria are entities absorbed from the intestinal tract, thus exhibiting immunopotentiating actions including inhibitory actions on the vascularization of tumors and extravasation of cancer cells. With this in mind, the inventors have paved the way for developing Panax saponins as absorbed entities of the saponins to be used as a novel type of anticancer agent, which is not affected by the differences of each intestinal bacteria group (ref: Korean Patent Application No. 4217 filed on 1996).

The process for the preparation of the above mentioned metabolites of Panax ginseng saponins, i.e., 20-O-$\beta$-D-glucopyranosyl-20(s)-protopanaxadiol, named compound K and 20-O-$\alpha$-L-arabinoopyranosyl(1$\rightarrow$6)-$\beta$-D-glucopyranosyl]-20(s)-protopanax adiol, named compound Y, has been already reported by utilizing some enzymes produced by the intestinal bacteria derived from *Aspergillus niger*, soil strain, rat's and the human's faeces [ref: Yoshioka, I.: Chem. Pharm. Bull., 20, 2418(1972), Kamida et al.; Pharmacology Journal, 95, 246(1975). Takino et al.: Medicinal ginseng 1989(Public Publications Co., Ltd.), 267 (1989), Kaneoka et al.; Japanese Herbal Medicine Journal, 11. 241(1994)]. Further, another method of manufacturing 20-O-[$\alpha$-L-arabinopuranosyl(1$\rightarrow$6)-$\beta$-D-glucopyranosyl]-20(s)-protopanaxadiol, named ginsenoside Mc, using intestinal bacteria derived from the human's faeces, has been also reported by the inventor(ref: Korean Patent No. 4217 filed on 1996).

The production of a compound K by the method of using soil strains requires more than 2-week cultivation. Further, in an enzymatic treatment method using crude Hesperidinase produced by *Aspergillus niger*, one of $\beta$-glucosidase, the compound K is produced since the intestinal bacteria in the metabolic route of ginseng saponin produce different enzymes but a compound Y and ginsenoside Mc are not nearly produced due to the production of ginsenoside F2.

Moreover, the method treated by the intestinal bacteria derived from the human's faeces has extended the production of their metabolites ranging from a compound Y and ginsenoside Mc to the compound K whereby their selectivity is low. As such, the conventional manufacturing method has recognized some disadvantages in that a) its production efficiency is low, and b) the selective production activity is low due to additional formation of the cleavable enzyme of sugar in addition to $\beta$-glucosidase. Under such circumstances, the prior arts are deemed not to be adequate in efficiently preparing the metabolite of this invention, compound K, compound Y and ginsenoside Mc.

SUMMARY OF THE INVENTION

To overcome the above mentioned shortcomings of the prior arts and prepare the metabolites of ginseng saponin in such as manner to ensure their selective production with high efficiency, therefore, the inventor has extensively studied an enzymatic induction method by which the intestinal bacterial group derived from the human's faeces is subjected to a successive passage culture in a medium containing ginsenoside Rb1 so as to facilitate the growth of bacteria producing $\beta$-glucosidase and in consequence, succeeded in isolating the strain S-1(Korean Culture Center of Microorganisms deposited on Nov. 8, 1996; its accession No.: KFCC-10923 and it's converted into the accession number : KCCM-10103 by the International Depository Authority under the Budapest Treaty, on Jul. 11, 1997.) producing $\beta$-glucosidase more actively from the subcultured bacteria. Through careful investigation on the morphological and biochemical appearances related to the strain S-1, its properties was in comparison with that specified in the literatures (Holdeman, L. V., Bergey's Mannual of Systematic Bacteriology, Williams and Wilkins, Vol. 1, 616–617(1984): Shar, H. N., Int. J. Syst. Bacteriol. 40, 205–208(1990)). Thus, it is noted that the strain S-1 belonging to Prevotella sp. of Bacteroidaceae is similar to *Prevotella oris*. Further, as a result of investigating the production of metabolites related to ginseng saponin using S-1 strain (KFCC-10923, it's converted into KCCM-10103 under Budapest Treaty) and *Prevotella oris* standard strain JCN 8540 (assigned by a microorganism storage facility of Japanese Physicochemical Research Institute), the standard strain does not exhibit any metabolic activity but the S-1 strain is effectively metabolized to give protopanaxadiol saponin so that a compound K, compound Y and ginsenoside Mc may be produced in such as manner to ensure their selective production with high efficiency. Now that the method of using the S-1 strain has proven to be quite useful in manufacturing the metabolites of this invention, this invention has been finally completed.

An object of this Invention is to provide a process for the preparation of a compound K, compound Y and ginsenoside Mc using Prevotella sp. strain (KFCC-10923, it's converted into the accession no.: KCCM-10103) with the following characteristics:

1) The strain is an obligate and asporogenic gram-negative rod-shaped bacterium.
2) The strain has no moiety, reduction of acetate and indole-producing activity.
3) The strain mainly produces succinic acid from glucose but without gas.
4) The growth of the strain is inhibited in peptone-yeast extract medium containing 20% bile.
5) The strain does not produce any pigments, when cultured in a blood agar medium.
6) The strain hydrolyzes starch and esculin.
7) The strain produces some acids from L-arabinose, D-xylose, D-glucose, D-mannose, D-fructose, maltose, sucrose, lactose and starch but not from trehalose, D-sorbitol, D-mannitol, inositol and L-rhamnose.

8) The strain hydrolyzes ginsenoside Rb1 and Rd and its main product is compound K. Further, the main products hydrolyzed from ginsenoside Rb2 and Rc are compound Y and ginsenoside Mc, respectively. However, ginsenoside Re and Rg1 are not nearly degradated.

Further, this invention may also include another process of manufacturing the ginsenoside Rb1-metabolized bacteria by the process of enzymatic induction; namely, the intestinal bacteria group derived from the human's faeces is subjected to a successive passage culture in a medium supplemented with about 0.1% of ginsenoside Rb1, thus making it possible to increase the production of β-glucosidase, which hydrolyses selectively the glucose at the terminal of sugar chain. After being treated the subcultured bacteria group with aminoglycoside antibiotics such as gentamicin, neomycin, kanamycin, etc., Prevotella sp. S-1 strain may be isolated on the basis that ginsenoside Rb1-metabolized bacteria are resistant to these antibiotics. Further, the strain may be isolated from enteric(intestinal) bacteria present in some animals (rats, mice, etc.).

Novel Prevotella sp. S-1 strain of this invention was deposited to the Korean Culture Center of Microorganisms (the KCCM) on Nov. 8, 1996. (its accession No.: KFCC-10923) and it's converted into the accession No. KCCM-10103 by the KCCM, International Depository Authority under Budapest Treaty.

Further, Panax ginseng saponin metabolites according to this invention is manufactured as follows:

Prevotella sp. S-1 strain (KFCC-10923 and it's converted into the accession no. KCCM-10103 under Budapest Treaty) is added in a liquid medium supplemented with protopanaxadiol saponin, so obtained by the well known method from the upper and lower stems of Korean Panax ginseng (Panax ginseng C. A. Meyer) and its tissue cultures. Then, the reacting mixture is anaerobically cultured at about 37° C. for 2–4 days and among sugars linked to hydroxy groups at 3- and 20-position of each saponin, its terminal glucose may be selectively removed by an enzymatic hydrolysis. The resulting solution, so cultured, is extracted with water-saturated n-Buthanol two times and after washing n-Buthanol part with water, the extract is treated with active carbon for discoloration and deodoring, and concentrated under reduced pressure. The residue is dissolved in ethyl acetate and purified on silica gel column chromatography (e.g., silica gel manufactured by Merck Co. Ltd., 60~230 mesh; elution solvent; ethyl acetate/chloroform:ethyl acetate: ethanol(60:30:10, lower layer), and silica gel RP-8 manufactured by Merck Co. Ltd.; elution solvent; 80~85% methanol) to give a compound K, compound Y and ginsenoside Mc.

By the procedure as described above, the metabolites of Panax ginseng saponin may be also obtained from Panax sp. plants such as Panax pseudo-ginseng Wall, Panax notoginseng Burk., Panax quinquefolium L., Panax japonicus C. A. Meyer, Panax pseudo-ginseng Wall. subsp. Himalaicus or Panax vietnamensis Ha et Grushv. They may be also obtained from other plants containing saponins with similar glycoside having a main structure of 20(s)-protopanaxadiol saponin [e.g., Amachazuru in the Cucurbitaceae family (Gynostemma pentaphyllum Makino and its near related plants)].

The process for manufacturing the metabolites of ginseng saponin using Prevotella sp. S-1 strain(KFCC-10923/KCCM-10103) according to this invention is explained in more detail by the following examples below, but this invention is not limited to these examples.

Reference example 1 g of faeces, collected from a healthy adult male, was suspended in a common-type anaerobic medium(e.g., GAM liquid medium, 30 ml) and anaerobically cultured overnight at about 37° C. The enteric(intestinal) bacteria derived from the human's faeces were subjected to a successive passage culture in GAM liquid medium containing ginsenoside Rb1(0.1%) at the intervals of 2 or 3 days. After elapse of 10 months, the diluted subculture solution was applied to GAM agar medium supplemented with gentamicin (100 μg/ml) and anaerobically cultured at about 37° C. for 2 days. All grown colonies of bacteria were collected by loop in terms of morphological type and among them, Prevotella sp. S-1 strain metabolized by ginsenoside Rb1 was isolated (KCCM deposited on Nov. 8, 1966 with its accession No. KFCC-10023 and it's converted into the accession no. KCCM-10103 under Budapest Treaty).

EXAMPLE 1

Prevotella sp. S-1 strain solution, previously cultured overnight in GAM liquid medium(100 ml), was added to Mueller-Hinton liquid medium(3 L) supplemented with ginsenoside Rb1 (0.2%) and then, was anaerobically cultured under nitrogen atmosphere at about 37° C. for 2 days. The resulting solution, so cultured, was extracted with water-saturated n-Buthanol (1 L) two times and after washing n-Buthanol part with water (1 L), the extract was treated with active carbon for discoloration and deodoring, and concentrated under reduced pressure. The residue was dissolved in ethyl acetate(500 ml) and purified on silica gel column chromatography(silica gel manufactured by Merck Co.; 60~230 mesh, 150 g). The resulted residue was washed with ethyl acetate (1 L) and eluted with elution solvent (chloroform:ethyl acetate:ethanol=60:30:10, 500 ml of lower layer). The solvent was removed under reduced pressure to give a crude metabolite (2.1 g). The crude metabolite was separated in a pure form by reverse-phase silica gel column chromatography [250 g of silica gel RP-8 manufactured by Merck Co.; elution solvent (85% methanol)] to give a compound K (1.5 g).

EXAMPLE 2

Prevotella sp. S-1 strain solution, previously cultured overnight in GAM liquid medium (100 ml), was added to Mueller-Hinton liquid medium (3 L) supplemented with ginsenoside Rb2 (0.2%) and then, was anaerobically cultured under nitrogen atmosphere at about 37° C. for 2 days. The resulting solution, so cultured, was extracted with water-saturated n-Buthanol (1 L) two times and after washing n-Buthanol part with water (1 L), the extract was treated with active carbon for discoloration and deodoring, and concentrated under reduced pressure. The residue was dissolved in ethyl acetate (500 ml) and purified on silica gel column chromatography (silica gel manufactured by Merck Co.; 60~230 mesh, 150 g). The resulted residue was washed with ethyl acetate (1 L) and eluted with elution solvent (chloroform:ethyl acetate:ethanol=60:30:10, 500 ml of lower layer). The solvent was removed under reduced pressure to give a crude metabolite (3.6 g). The crude metabolite was separated in a pure form by reverse-phase silica gel column chromatography [250 g of silica gel RP-8 manufactured by Merck Co.; elution solvent (80% methanol)] to give a compound Y (3.1 g).

EXAMPLE 3

Prevotella sp. S-1 strain solution, previously cultured overnight in GAM liquid medium (100 ml), was added to Mueller-Hinton liquid medium (3 L) supplemented with ginsenoside Rc (0.2%) and then, was anaerobically cultured under nitrogen atmosphere at about 37° C. for 2 days. The resulting solution, so cultured, was extracted with water-saturated n-Buthanol (1 L) two times and after washing n-Buthanol part with water (1 L), the extract was treated with active carbon for discoloration and deodoring, and concentrated under reduced pressure. The residue was dissolved in ethyl acetate (500 ml) and purified on silica gel column chromatography (silica gel manufactured by Merck Co.; 60~230 mesh, 150 g). The resulted residue was washed with ethyl acetate (1 L) and eluted with elution solvent (chloroform:ethyl acetate:ethanol=60:30:10, 500 ml of lower layer). The solvent was removed under reduced pressure to give a crude metabolite (3.6 g). The crude metabolite was separated in a pure form by reverse-phase silica gel column chromatography [250 g of silica gel RP-8 manufactured by Merck Co.; elution solvent (80% methanol)] to give a compound Mc (3.6 g).

EXAMPLE 4

Prevotella sp. S-1 strain solution, previously cultured overnight in GAM liquid medium (30 ml), was added to Mueller-Hinton liquid medium (1 L) supplemented with protopanaxadiol saponin (0.3 %) and then, was anaerobically cultured under a nitrogen atmosphere at about 37° C. for 2 days. The resulting solution, so cultured, was extracted with water-saturated n-Buthanol (1 L) two times and after washing n-Buthanol part with water (300 ml), the extract was treated with active carbon for discoloration and deodoring, and concentrated under reduced pressure. The residue was dissolved in ethyl acetate (200 ml) and purified on silica gel column chromatography (silica gel manufactured by Merck Co.; 60~230 mesh, 50 g). The resulted residue was washed with ethyl acetate (300 ml) and eluted with elution solvent (chloroform:ethyl acetate:ethanol 60:30:10, 500 ml of lower layer). The solvent was removed under reduced pressure to give a crude metabolite (1.1 g). The crude metabolite was separated in a pure form by reverse-phase silica gel column chromatography [250 g of silica gel RP-8 manufactured by Merck Co.; elution solvent (80–85% methanol)] to give a compound K (0.6 g), compound Y (0.1 g) and ginsenoside Mc (0.2 g) in a sequential order.

As noted in the above mentioned examples, the process for manufacturing the metabolites of ginseng saponin using Prevotella sp. S-1 strain (KFCC-10923/KCCM-10103) has proven to be quite effective in that the protopanaxadiol saponin metabolites—compound K, compound Y and ginsenoside Mc—may be prepared in such as manner to ensure their selective production with high efficiency.

What is claimed is:

1. An isolated strain of microorganism having the Accession Number KCCM 10103, said strain having the following characteristics:
   the strain is an obligate-aerobic, asporogenous, gram-negative, rod-shaped bacterium;
   the strain lacks motility, fails to reduce acetates and lacks indole-producing activity;
   the strain mainly produces succinic acid from glucose but fails to produce gas;
   the growth of the strain is inhibited in a peptone-yeast extract medium containing 20% bile juice;
   the strain fails to produce pigments, when cultured in a blood agar medium;
   the strain hydrolyzes starch and esculin; and
   the strain produces some acids from L-arabinose, D-xylose, D-glucose, D-mannose, D-fructose, maltose, sucrose, lactose and starch but not from trehalose, D-sorbitol, D-mannitol, inositol and L-rhamnose;
   the strain hydrolyzes ginsenoside Rb1 and Rd and the resulting main product is 20-O-β-D-glucopyranosyl-20 (s)-protopanaxadiol and the main products hydrolyzed from ginsenoside Rb2 and Rc are 20-O-[α-L-arabinopyranosyl(1→6)-β-D-glucopyranosy]-20(s)-protoopanax adiol and 20-O-[α-L-arabinopuranosyl (1→6)-β-D-glucopyranosyl]-20(s)-protopanaxadiol, respectively and fails to degrade ginsenoside Re and Rg1.

2. The microorganism of claim 1 which is obtained by subjecting the intestinal bacterial group of human feces to successive passage culture in a medium containing ginsenoside Rb1 and subsequent treatment with a suitable aminoglycoside antibiotic selected from a group consisting of gentamicin, neomycin and kanamycin, etc.

3. The microorganism of claim 1, wherein the strain is unable to degrade ginsenoside Re and Rg1.

4. The microorganism of claim 1, wherein the strain is Prevotella sp S-1 strain.

5. A process for the preparation of metabolites of protopanaxadiol saponin, comprising culturing the microorganism of claim 4 of Prevotella sp. S-1 strain in a medium supplemented with Panax ginseng saponin; and generating and collecting 20-O-β-D-glucopyranosyl-20(s)-protopanaxadiol, 20-O-[-α-L-arabinopyranosyl (1→6) -β-D-glucopyranosyl]-20(s)-protopanaxadiol and 20-O-[α-L-arabinopuranosyl(1→6)-β-D-glucopyranosyl]-20(s)-protopanaxadiol contained in the medium.

6. A process for the preparation of the metabolites of protopanaxadiol saponin according to claim 5 wherein the ginseng saponin is sourced from plants that are selected from a group consisting of Panax ginseng C. A. Meyer, Panax pseudo-ginseng Wall, Panax notoginseng Burk., Panax quinquefolium L., Panax japonicus C. A. Meyer, Panax pseudo-ginseng Wall. subsp. Himalaicus or Panax vietnamensis Ha et Grushv., or Amachazuru saponin of the cucurbitaceae family.

* * * * *